United States Patent
Furusawa et al.

(10) Patent No.: US 6,371,908 B1
(45) Date of Patent: Apr. 16, 2002

(54) VIDEO ENDOSCOPIC APPARATUS FOR FLUORESCENT DIAGNOSIS

(75) Inventors: Koichi Furusawa, Tokyo; Tetsuya Utsui, Saitama-ken, both of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/301,546

(22) Filed: Apr. 29, 1999

(30) Foreign Application Priority Data

May 1, 1998 (JP) ............................................ 10-122561

(51) Int. Cl.⁷ .............................. A61B 1/04; A61B 6/00
(52) U.S. Cl. ........................................ 600/160; 600/477
(58) Field of Search ................................ 600/109, 160, 600/178, 476–478, 407; 250/458.1

(56) References Cited

U.S. PATENT DOCUMENTS

| | | | | |
|---|---|---|---|---|
| 5,363,854 A | * | 11/1994 | Martens et al. | ............. 600/407 |
| 5,408,996 A | * | 4/1995 | Salb | ........................... 600/478 |
| 5,591,981 A | * | 1/1997 | Heffelfinger et al. | .... 250/458.1 |
| 5,986,271 A | * | 11/1999 | Lazarev et al. | .......... 250/458.1 |
| 5,999,844 A | * | 12/1999 | Gombrich et al. | .......... 600/476 |
| 6,104,939 A | * | 8/2000 | Groner et al. | .............. 600/476 |
| 6,161,031 A | * | 12/2000 | Hochman et al. | ........... 600/407 |

* cited by examiner

Primary Examiner—John P. Leubecker
(74) Attorney, Agent, or Firm—Greenblum & Bernstein, P.L.C.

(57) ABSTRACT

Data of ordinary color observation image obtained by picking up an object according to a RGB flame sequential system and data of fluorescent observation image obtained when the object is irradiated with excitation light are respectively transmitted to the PC. The PC calculates luminance values based on the data of ordinary color observation image to extract an area where luminance is higher than a first threshold, and extracts areas where luminance is lower than second threshold which is higher than the first threshold from the data of fluorescent observation image. The PC specifies an area which is included in both of these extracted areas, as an area having a high possibility of indicating an abnormal area.

9 Claims, 8 Drawing Sheets

VIDEO ENDOSCOPIC APPARATUS FOR FLUORESCENT DIAGNOSIS

BACKGROUND OF THE INVENTION

1. Field of the Invention

The present invention relates to a video endoscopic apparatus for fluorescent diagnosis which picks up interior of a body cavity on the basis of auto-fluorescent light emitted from a living body to output image data used to diagnose whether the living body is normal or abnormal. The present disclosure relates to subject matter contained in Japanese Patent Application No. Hei10-122561 (filed on May 1, 1998), which is expressly incorporated herein by reference in its entirety.

2. Description of the Related Art

It is known that fluorescent light which is called "auto-fluorescent light" is emitted from a living body when excitation light of a specific wavelength is irradiated upon the living body. Further, it is also known that since an abnormal part (tumor, cancer) of the living body is lower in intensity of auto-fluorescent light within wavelength band of green light than a normal part, the abnormal part is displayed darker than the normal part when it is formed into an image. There has been proposed a video endoscopic apparatus for fluorescent diagnosis which picks up the auto-fluorescent light emitted from the living body and displays an auto-fluorescent image of the living body available for diagnosing whether the living body is normal or abnormal, on the basis of such knowledge. One of those examples is disclosed in Japanese Patent Application Laid-Open No. 9-70384. In a video endoscopic apparatus for fluorescent diagnosis disclosed in the description, there is provided an image intensifier for amplifying the auto-fluorescent light between an objective optical system and an image sensor at the distal end of the video endoscope, taking it into consideration that the auto-fluorescent light is very weak. Therefore, according to this video endoscopic apparatus for fluorescent diagnosis, a bright auto-fluorescent image can be obtained because the auto-fluorescent image amplified by the image intensifier is picked up by an imaging device.

However, the outside diameter of the distal end of an insertion portion of the video endoscope must be large enough to contain the image intensifier. The distal end is inserted into the body cavity of a patient, so that there is a problem that a load of pain is imposed on the patient in case the distal end is too large. Also, since the image intensifier is comparatively expensive, there is a problem that the cost of the entire video endoscopic apparatus for fluorescent diagnosis will be increased if the image intensifier is installed at the distal end of the video endoscope.

SUMMARY OF THE INVENTION

It is an object of the present invention to provide a video endoscopic apparatus for fluorescent diagnosis capable of obtaining an appropriate image for fluorescent diagnosis even if any image intensifier is not used.

In the present invention, the following construction is adopted to achieve the above object.

A video endoscopic apparatus for fluorescent diagnosis in a first aspect of the present invention comprises a image pick-up device which picks up an auto-fluorescent image generated by irradiating excitation light onto a living body, a detection unit which detects a specific area where luminance value is within a predetermined range from the auto-fluorescent image picked up by the foregoing image pick-up device and a display control device which outputs an image signal indicating the specific area.

The apparatus being constructed in this way, the detection unit extracts the specific area from the auto-fluorescent image, and the display control device outputs an image signal indicating this specific area. Therefore, an image indicating shape and position of this specific area can be displayed on a display unit such as CRT or a liquid crystal display. Accordingly, if the range of luminance value covers that of the specific area is set to a range including the luminance value of auto-fluorescent light emitted from an abnormal part of the living body, the abnormal part is displayed as the specific area. For this reason, even if no image intensifier is provided, an appropriate image for fluorescent diagnosis can be supplied to a user (doctor or the like) of the video endoscopic apparatus for fluorescent diagnosis, so that the user can appropriately diagnose on the basis of the auto-fluorescent light. The detection unit and the display control device can be constructed, for example, as functions of a CPU (Central Processing Unit) executing a program or as an LSI, ASIC or the like.

A second aspect of the present invention is characterized in that the detection unit has a first extracting unit which extracts an area where luminance value is higher than a predetermined first threshold from the auto-fluorescent image and a second extracting unit which extracts, as the specific area, an area where luminance value is lower than a predetermined second threshold from the area extracted by the first extracting unit.

A third aspect of the present invention is characterized in that the image pick-up device has an illuminating device selectively emitting illuminating light in a visible band and excitation light in a ultraviolet band to irradiate a living body, and picks up a nomal color observation image of the foregoing living body irradiated with illuminating light in the visible band and an auto-fluorescent image of the living body irradiated with the excitation light respectively, and in that the detection unit extracts an area where luminance value is higher than the first threshold from the ordinary color observation image, extracts an area where luminance value is lower than the second threshold from the auto-fluorescent image, and detects, from area extracted from the nomal color observation image, an area included in the area extracted from the auto-fluorescent image as the specific area.

A fourth aspect of the present invention is characterized in that the display control device outputs an image signal for displaying a fluorescent observation image, in which only the specific area is indicated in a predetermined color. When constructed in this way, if there is an abnormal part in a living body as the object, the abnormal part is displayed in a predetermined color as a specific area in a fluoresecnt diagnosis image. For this reason, the user can easily diagnose whether or not it is an abnormal part.

A fifth aspect of the present invention is characterized in that the display control device outputs an image signal for displaying a fluorescent observation image, in which only the specific area is displayed in a predetermined color and the other area is displayed in color. The fluorescent observation image may be entirely displayed in monochrome. Also, the other area than the specific area within the fluorescent observation image may be displayed in pseudocolor. However, if only the specific area is displayed in a predetermined color and the other area than the specific area is displayed in color, the diagnosis will become more easier.

A sixth aspect of the present invention is characterized in that the pick-up device irradiates the living body with each illuminating light of red, green and blue in order, and at the same time, picks up images of the living body respectively irradiated with each illuminating light, and in that the display control device synthesizes the ordinary color image on the basis of images of the living body irradiated with the respective illuminating light, generates specific area image of the specific area extracted from the auto-fluorescent image and outputs image signal for displaying a fluorescent observation image comprising the specific area image superimposed on the ordinary color observation image.

A seventh aspect of the present invention is characterized in that the above-described display control device outputs image signal for displaying both of the ordinary color observation image and the fluorescent observation image at the same time. When constructed in this way, the user can easily diagnosis normality or abnormality of a living body because the user can observe two images while comparing them.

An eighth aspect of the present invention is characterized in that the display control device outputs an image signal for displaying the ordinary color observation image as a moving picture.

A ninth aspect of the present invention further comprises a switch, which is operated by an operator to generate a switching signal for causing the display control device to output an image signal for displaying only the ordinary color observation image or an image signal for displaying the ordinary color observation image and the fluorescent diagnosis image at the same time respectively.

BRIEF DESCRIPTION OF THE DRAWINGS

The invention will be described in detail with reference to the accompanying drawings, in which.

DESCRIPTION OF PREFERRED EMBODIMENT

Configuration of Video Endoscopic Apparatus

Figure 1:
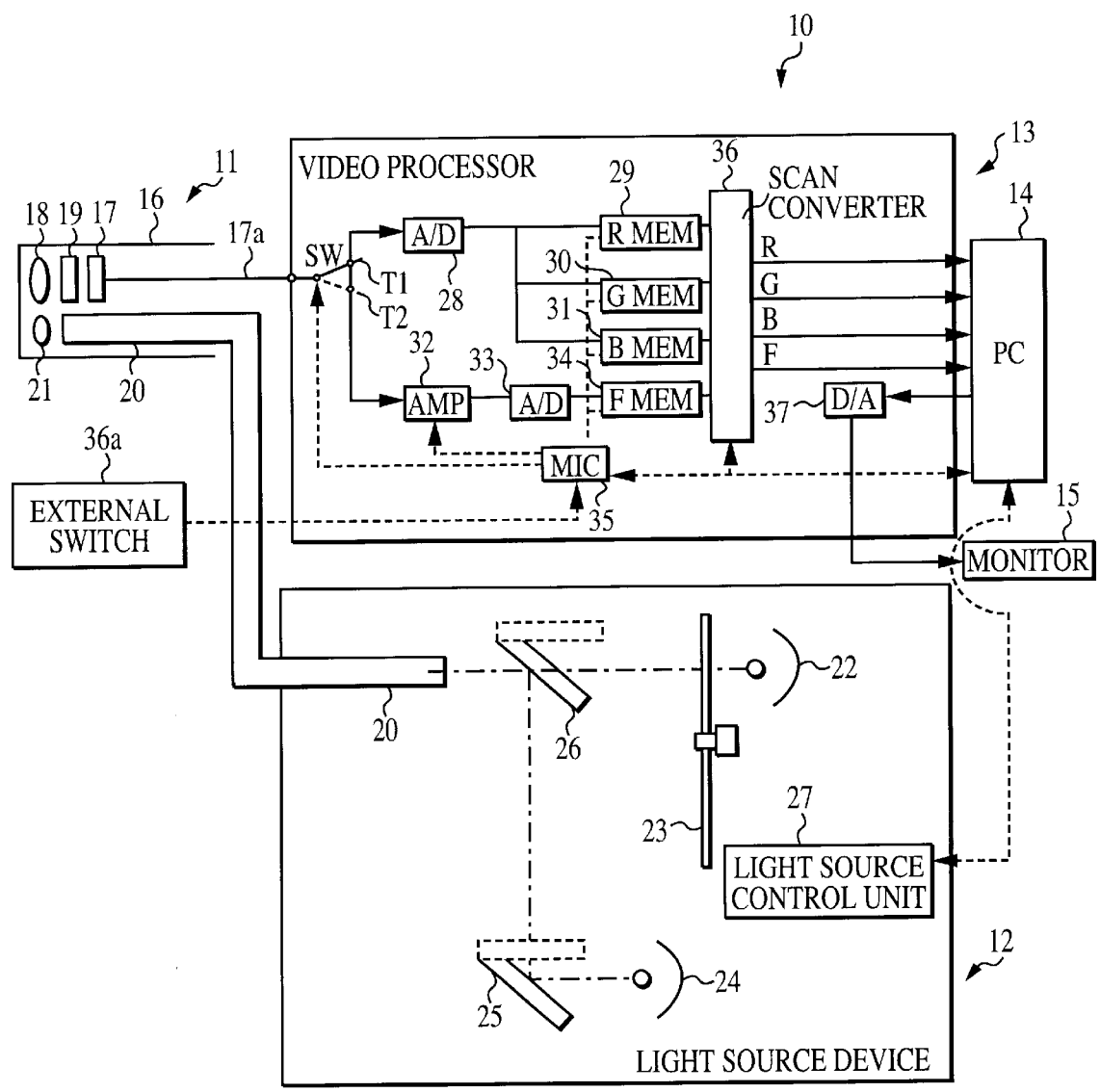
FIG. 1 is a block diagram showing a video endoscopic apparatus for fluorescent diagnosis according to an embodiment of the present invention.

FIG. 1 is a schematic block diagram showing a video endoscopic apparatus for fluorescent diagnosis (hereinafter, referred to as simply "video endoscopic apparatus") 10 according to an embodiment of the present invention. As shown in FIG. 1, the video endoscopic apparatus 10 comprises a video endoscope 11, a light source device 12 and a video processor 13 which are connected to the video endoscope 11, and a personal computer (PC) 14 and a monitor 15 which are connected to the video processor 13. Hereinafter, these devices will be described individually.

Although only an insertion portion 16 is shown in FIG. 1, the video endoscope 11 actually comprises an operating portion which is provided with a dial for bending a bending portion provided at vicinity of a distal end of the insertion portion 16 and various operating switches. Further the video endoscope 11 comprises various components such as a light guide flexible tube connected to a light source device 12. The insertion portion 16 shown in FIG. 1 is inserted into a body cavity of a patient. Distal end of the insertion portion 16 is fixed with a distal end part (not shown) made of a rigid member in which at least two through-holes are bored along the axial direction thereof. At the openings of these two through-holes on the distal end side of the insertion portion 16, there are embedded an objective optical system 18 and a light distribution lens 21 respectively. The objective optical system 18 forms an image of an object. At the rear side (proximal end side) of the objective optical system 18, a cut-off filter 19 and a solid state image sensor (CCD) 17 are fixed in order. This cut-off filter 19 interrupts excitation light which is reflected by the inner surface of the body cavity as an object and transmits through the objective optical system 18, when excitation light (ultraviolet rays) for exciting an auto-fluorescent light is irradiated onto the object. The CCD 17 is arranged at a position where an image of the object is formed by the objective optical system 18, and is connected to the video processor 13 through a signal cable 17a. An image signal obtained when the CCD17 picks up the object image formed by the objective optical system 18 is inputted into the video processor 13 through the signal cable 17a to be processed by the video processor 13. On the other hand, on the proximal end side of the light distribution lens 21, there is arranged an emitting end surface of a light guide fiber bundle (hereinafter, referred to as "light guide") 20 extended into the insertion portion 16 through the light guide flexible tube and the operating portion of the video endoscope 11. Since the incident end face of this light guide 20 is arranged within a light source device 12, the light guide 20 transmits illuminating light supplied from the light source device 12 to the distal end of the insertion portion 16. Illuminating light emitted from the emitting end face of the light guide 20 is diffused by the light distribution lens 21 to illuminate an area of object which can be picked up by the objective optical system 18 and the CCD17.

The light source device 12 contains a white light source 22 to supply illuminating light to the light guide 20. The white light source 22 is made up of a lamp which emits white light as illuminating light for ordinary color observation, and a reflector which converges the white light emitted from the lamp. An incident end face of the above-described light guide 20 is arranged at a position where white light is converged on the optical axis of the reflector of the white light source 22, and therefore, illuminating light emitted from the white light source 22 is effectively incident into the light guide 20. On the optical path of illuminating light between the white color source 22 and the light guide 20, there is arranged a RGB rotary filter 23. The RGB rotary filter 23 is embedded with three color filters having colors of R (red), G (green) and B (blue) respectively and having plane shape of sector with equal angle. These color filters are divided with one another by shading portions. The RGB rotary filter 23 is rotated at constant speed by a motor (not shown) so that each color filter embedded in the RGB rotary filter 23 is repeatedly inserted in the optical path of illuminating light emitted from the white light source 22 in order of R, G and B. Thus, each illuminating light of R light, G light and B light is repeatedly incident into the incident end face of the light guide 20, and is emitted from the distal end of the insertion portion 16 through the light guide 20 to illuminate the object through the light distribution lens 21. Thus, an image of an object illuminated with each illuminating light of R, G and B formed by the objective optical system 18 is picked up by the CCD17, and is synthesized as a ordinary color image by the video processor 13. In such away, ordinary color image of the object is picked up in accordance with the so-called RGB frame sequential system.

Further, within the light source device 12, there are provided a light source (UV light source) 24 consisting of a lamp for emitting ultraviolet rays as excitation light for auto-fluorescent light and a reflector for converging excitation light emitted from the lamp, and a first mirror 25 and a second mirror 26 which guide excitation light emitted from the UV light source 24 to the incident end face of the light guide 20. This first mirror 25 is arranged so as to be retracted from the optical path of excitation light emitted from the UV light source 24 at the time of ordinary color image observation, and to be inserted into the optical path of the excitation light to reflect the excitation light toward the second mirror 26 at the time of fluorescent diagnosis. The second mirror 26 is arranged so as to be retracted from the optical path of illuminating light emitted from the white light source 22 at the time of ordinary color image observation, and to be inserted into the optical path of the illuminating light between the RGB rotary filter 23 and the light guide 20 at the time of fluorescent diagnosis. When inserted into the optical path, the second mirror 26 interrupts the illuminating light from the white light source 22, and reflects the excitation light reflected by the first mirror 25 toward the incident end face of the light guide 20. With the foregoing configuration, illuminating lights (R light, G light and B light) which have passed through the RGB rotary filter 23 are incident into the incident end face of the light guide 20 at the time of ordinary color image observation, and excitation light emitted from the UV light source 24 is incident into the incident end face of the light guide 20 at the time of fluorescent diagnosis.

Further, the light source device 12 has a light source control unit 27. This light source control unit 27 adjusts, in accordance with an instruction from, for example, PC14, light amounts of illuminating light and excitation light which are incident into the light guide 20, and controls operations of the white light source 22, the RGB rotary filter 23, the first mirror 25 and the second mirror 26. Also, the light source control unit 27 supplies, to the PC14, a signal (synchronizing signal) indicating timing at which each of color filters of R, G and B passes through the optical path of illuminating light emitted from the white light source 22.

The video processor 13 has a switch SW connected to the signal cable 17a. The switch SW comprises two output terminals T1, T2 and an input terminal conducting with a switch piece capable of selectively contacting each output terminal T1, T2, and is actually constructed as an electronic circuit equivalent to a switch of such constructure. The switch piece of the switch SW comes into contact with the output terminal T1 at the time of ordinary color image observation, and comes into contact with the output terminal T2 at the time of fluorescent diagnosis. The output terminal T1 of the switch SW is connected to the input terminal of an analog-digital converter (A-D converter) 28. This A-D converter 28 converts form of signal (that is, image signal) outputted from the CCD17 during the time of ordinary color image observation from analog to digital and outputs the converted digital signal to its output terminal. The output terminal of this A-D converter 28 is connected to respective input terminals of a R memory 29, a G memory 30 and a B memory 31. The R memory 29 stores an image signal(which will be called "R image signal" hereinafter) outputted from the CCD17 when R light is irradiated onto the object. The G memory 30 stores an image signal (which will be called "G image signal" hereinafter) outputted from the CCD17 when G light is irradiated onto the object. Also, The B memory 31 stores an image signal(which will be called "B image signal" hereinafter) outputted from the CCD17 when B light is irradiated onto the object. On the other hand, the output terminal T2 of the switch SW is connected to an input terminal of an amplifier 32. This amplifier 32 amplifies an image signal (which will be called "F image signal" hereinafter) outputted from the CCD17 and outputs the amplified signal to its output terminal. The output terminal of this amplifier 32 is connected to the input terminal of the A-D converter 33. The A-D converter 33 converts form of the F image signal amplified by the amplifier 32 from analog to digital and outputs the digital signal to its output terminal. The output terminal of the A-D converter 33 is connected to the input terminal of the F memory 34. This F memory 34 stores the F image signal outputted from the A-D converter 33. Each output terminal of these R memory 29, G memory 30, B memory 31 and F memory 34 is connected to a scan converter 36. Each output terminal of the scan converter 36 is connected to the PC 14. In accordance with a synchronizing signal outputted from the PC14, this scan converter 36 reads out each image signal stored in the R memory 29, the G memory 30 and B memory 31, and outputs to the PC14 in synchronization with the synchronizing signal. Similarly, the scan converter 36 reads out the F image signal from the F memory 34 in accordance with the synchronizing signal inputted from the PC14 to output to the PC14.

Further, the video processor 13 has a microcomputer (MIC) 35 which is connected to the PC14, an external switch 36a provided outside of the video processor 13, the switch SW, the amplifier 32 and each control terminal of the R memory 29, the G memory 30, the B memory 31 and the F memory 34. In accordance with a control instruction from the PC14, this MIC35 makes the switch piece of the switch SW selectively come into contact with either the output terminal T1 or the output terminal T2. Also, in accordance with a control instruction from the PC14, the MIC35 adjusts gain of the amplifier 32. Also, in accordance with a synchronizing signal inputted from the PC14, the MIC35 makes an output signal from each A-D converter 28, 33 stored in the appropriate memory among the R memory, the G memory, the B memory and the F memory.

Further, the video processor 13 has a digital-analog converter (D-A converter) 37 connected to the PC14. The D-A converter 37 converts form of a RGB image signal outputted from the PC14 from digital to analog and inputs the analog RGB image signal into a monitor 15. Thus, the monitor 15 displays an image of the object on the basis of the analog RGB image signal.

Figure 2:
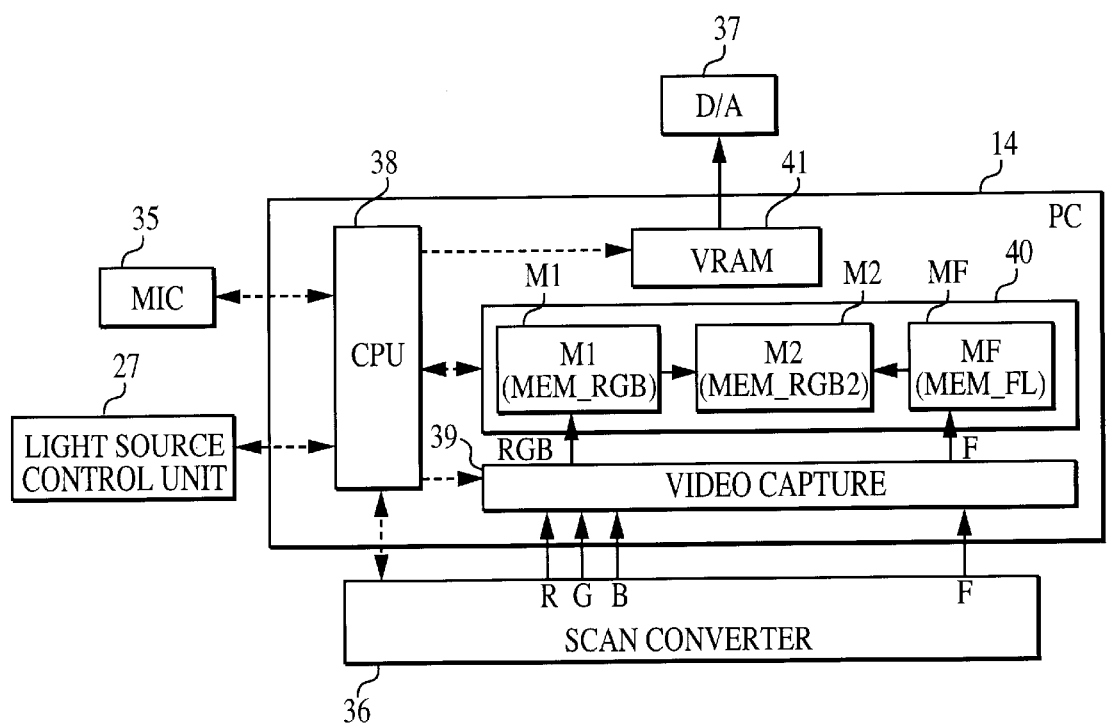
FIG. 2 is a block diagram showing the PC shown in FIG. 1.

The PC14 is a computer which further processes each image signal outputted from the video processor 13. This PC 14 comprises a CPU (Central Processing Unit) 38 which is connected to a light source control unit 27 in the light source device 12, the MIC35 and the scan converter 36 in the video processor 13, a video capture 39, a memory unit 40 and a VRAM (video RAM) 41, as shown in a block diagram of FIG. 2 in detail. The video capture 39 temporarily stores each of R image signal, G image signal, B image signal and F image signal outputted from a scan converter 36 in the video processor 13 and inputs the stored image signals into the memory unit 40, in accordance with an instruction form the CPU38. The memory unit 40 is a RAM (Random Access Memory) which is used for processing by the CPU38 and which is divided into a memory M1 (mem_RGB) area for storing each image signal of RGB outputted from the video capture 39, a memory MF (mem_FL) area for storing F image signals outputted from the video capture 39, and a memory M2 (mem_RGB2) used for forming and processing images for fluorescent diagnosis. The VRAM41 holds data (RGB image signal) which indicates the picture to be displayed on the monitor 15 and which is outputted from the CPU38, and outputs the RGB image signal to the D-A converter 37 in accordance with an instruction from the CPU38. The CPU38 executes a control program stored in an unillustrated ROM (Read Only Memory) to thereby control operations of the light source control unit 27, the MIC35, the video capture 39, the memory unit 40 and the VRAM41.

Figure 3:
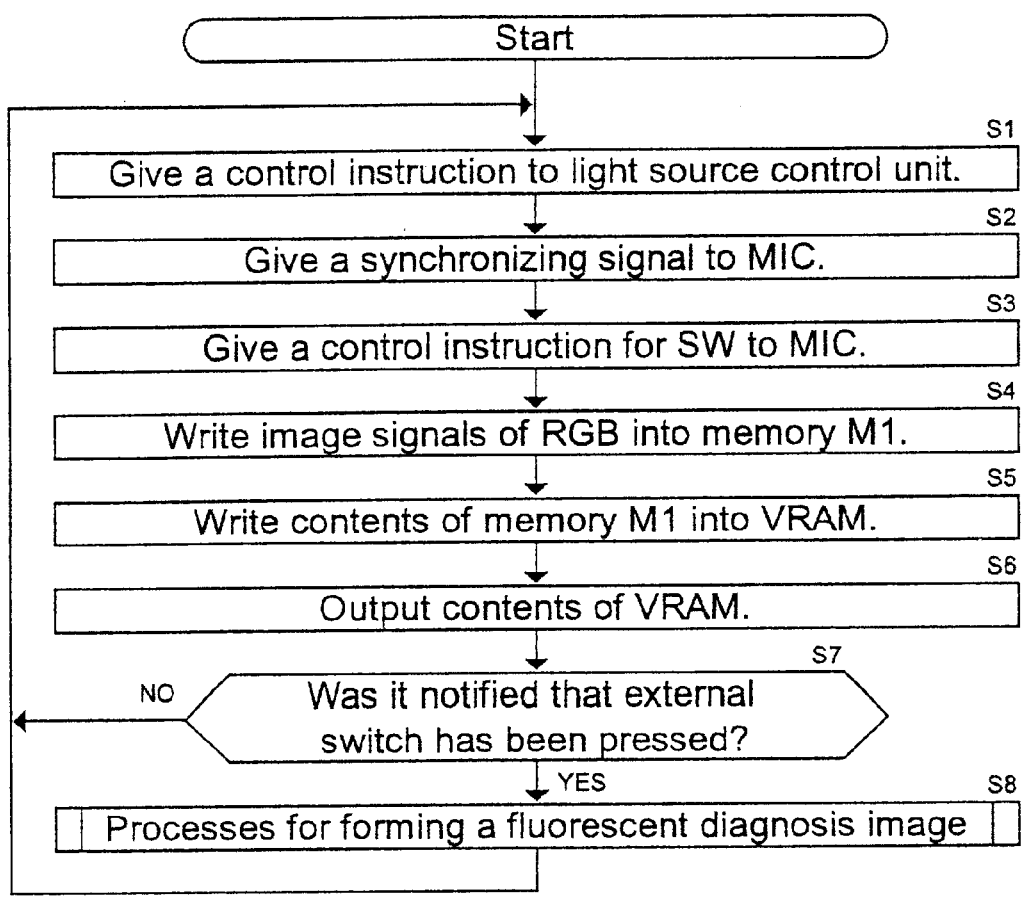
FIG. 3 is a flow chart showing a main routine of a processes executed by the CPU shown in FIG. 2.
Figure 4:
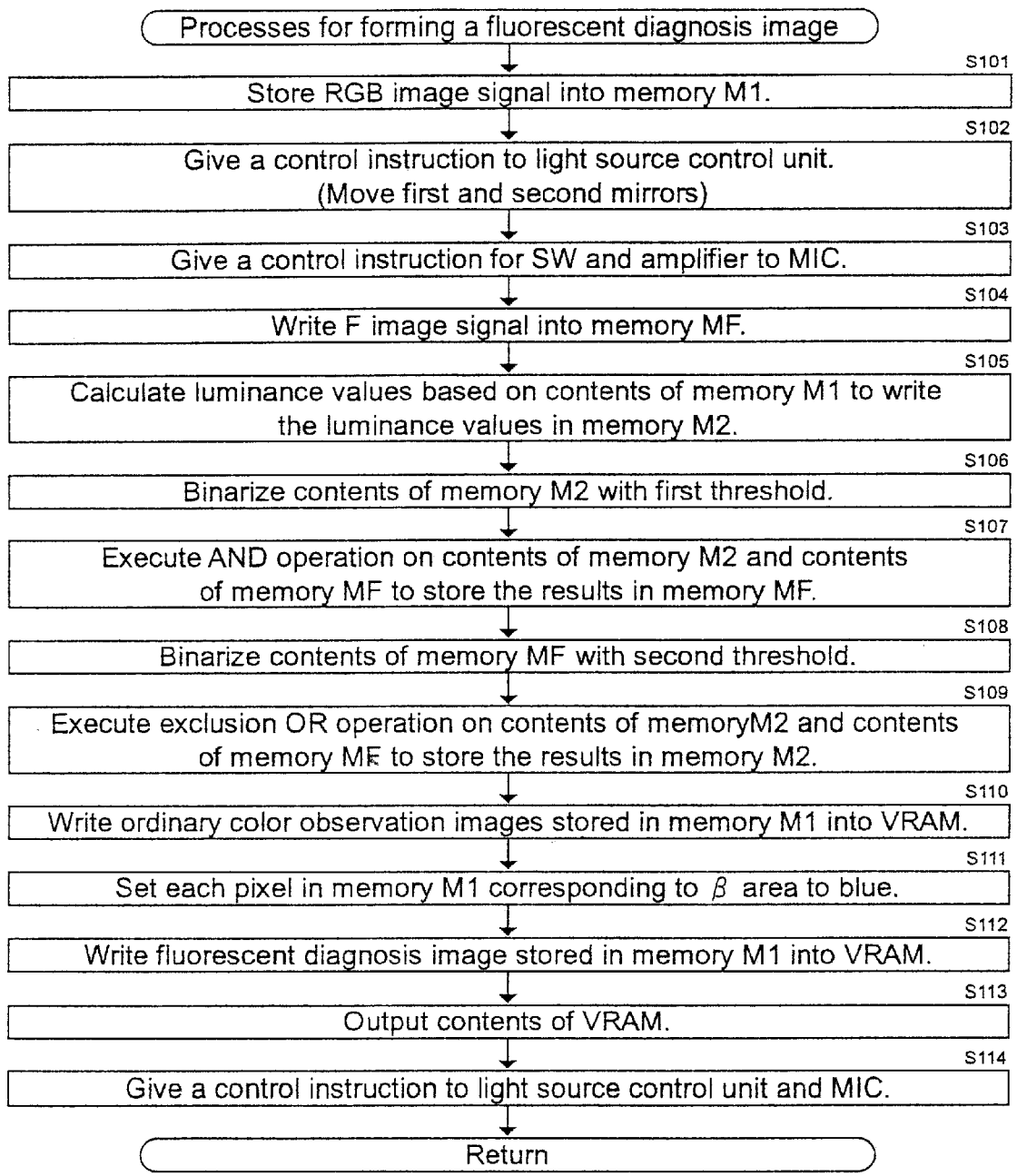
FIG. 4 is a flow chart showing a sub-routine of processes for forming a fluoresecnt diagnosis image.

Hereinafter, the description will be made of an example of the operation of a video endoscopic apparatus comprising each device having the above-described construction along the processing of the CPU38 in the PC14. FIG. 3 is a flow chart showing processes (main routine) executed by the CPU38, and FIG. 4 is a flow chart showing a subroutine of processes for forming the images for fluoresecnt diagnosis which are executed in S8 of FIG. 3. The processing shown in FIG. 3 is started when the main power supply for the light source 12, the video processor 13 and the PC14 are turned on respectively. After the starting, the CPU38 first gives the light source control unit 27 a control instruction for making the light source device 12 function in ordinary color image observation state (S1). Then, the light source control unit 27 in the light source device 12 retracts the first mirror 25 from the optical path of excitation light emitted from the UV light source 24, and at the same time, retracts the second mirror 26 from the optical path of illuminating light emitted from the white light source 22 (See broken line in FIG. 1). Subsequently, the light source control unit 27 makes the white light source 22 and the UV light source 24 light and makes the RGB rotary filter 23 rotate. As a result, the light source control unit 27 imparts a synchronizing signal of the RGB rotary filter to the CPU38. Then, the CPU38 distributes this synchronizing signal to the MIC35 and the scan converter 36 (S2). Besides, the CPU38 gives the MIC35 a control instruction to bring the switch piece of the switch SW into contact with the output terminal T1 (S3). Receiving this instruction, the MIC35 brings the switch piece of the switch SW into contact with the output terminal T1.

The processes of S1 through S3 is thus executed, whereby white illuminating light is emitted from the white light source 22. This white illuminating light passes through the RGB rotary filter 23 to thereby turn into each illuminating light of R light, G light and B light, and these illuminating lights are incident into the light guide 20 in order. The illuminating light of each color is transmitted to the distal end part of the video endoscope 11 through the light guide 20, then emitted from the emitting end face of the light guide, and illuminates the object (that is, internal surface of the body cavity) in order while diffused by the light distribution lens 21. When the object is irradiated by respective illuminating light in order, the reflected light from the object is focused and converged as an image of the object on the pick-up surface of the CCD17 by the objective optical system 18, and this object image is picked up by the CCD17. Then, image signals (R image signal, G image signal and B image signal) caused by each illuminating light are outputted in order from the CCD17. Each image signal is inputted into the A-D converter 28 through the signal cable 17a and the switch SW, then converted from analog signal to digital signal by the A-D converter 28, and thereafter inputted to the input terminals of each memory 29, 30, 31. At this time, on the basis of a synchronizing signal from the CPU38, the MIC35 inputs a control signal to the control terminals of each memory 29, 30, 31 in order. When this control signal is inputted, each memory 29, 30, 31 captures an image signal outputted from the A-D converter 28 at the point of time, and keeps to hold the image signal until the next control signal is inputted. Accordingly, the R image signal is stored in the R memory 29, the G image signal is stored in the G memory 30, and the B image signal is stored in the B memory 31. Thus, each image signal of RGB for one screen is stored in the R memory 29, the G memory 30 and the B memory 31 respectively. Then, the scan converter 36 reads out image signals of R, G and B from respective memories 29 through 31 and outputs these image signals toward the PC14 in synchronization with each other. Each image signal of R, G and B thus transmitted to the PC14 is stored in the video capture 39 of the PC14. Then, the CPU38 writes the image signals of R, G and B stored in the video capture 39 into the a memory M1 in the memory unit 40 (S4). As a result, a 24-bit RGB image signal (data of the ordinary color observation image) is synthesized on the memory M1, which is an aggregate of multiple pixels each of which is composed of R image signal, G image signal and B image signal each having respective luminance value of 8 bits.

Figure 5:
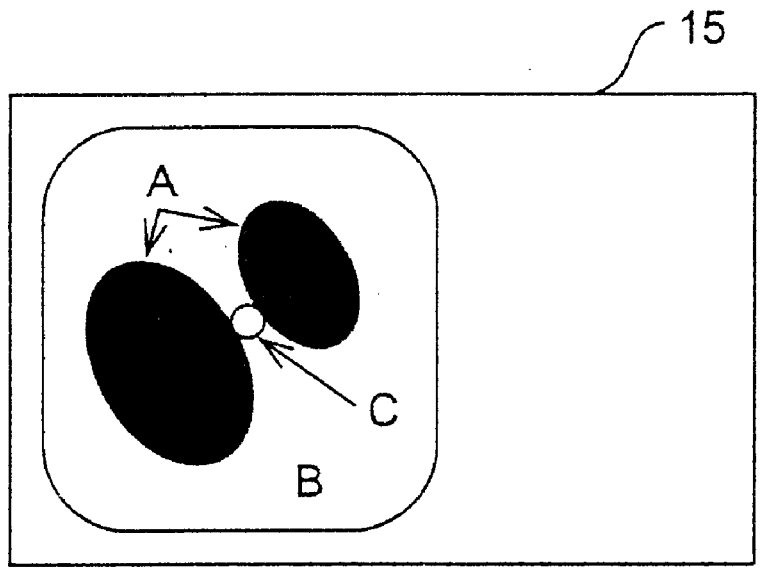
FIG. 5 is a view showing a display example of a ordinary color observation image.
Figure 6:
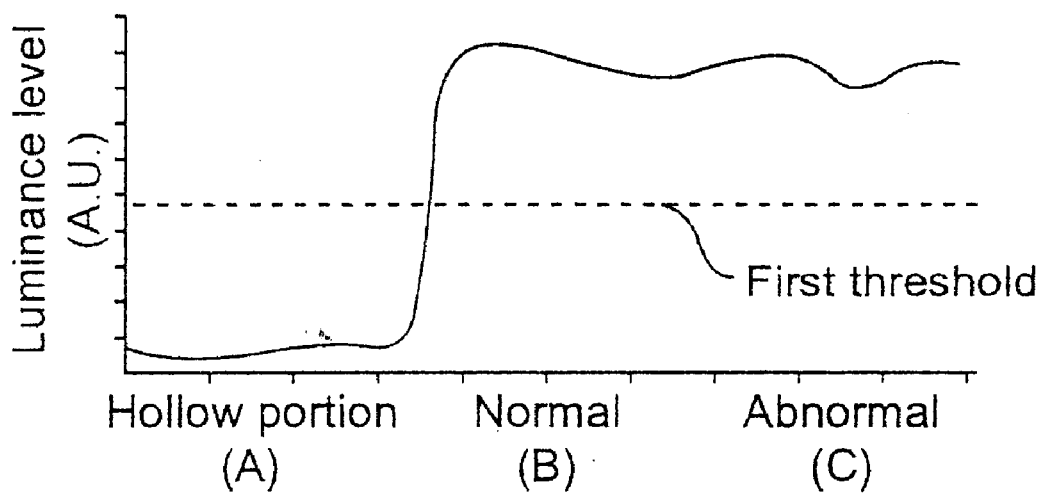
FIG. 6 is a graph showing luminance distribution in the ordinary color observation image.

Subsequently, the CPU38 reads out the RGB image signal (that is, data of the ordinary color observation image) stored in the memory M1 to write it into the VRAM41 (S5). Subsequently, the CPU38 makes the RGB image signal stored in the VRAM41 outputted toward the D-A converter 37 (S6). Then, the D-A converter 37 converts the form of the RGB image signal outputted from the VRAM41 from digital to analog and supplies the converted signal to the monitor 15. Thus, as shown in FIG. 5, on a display area of the monitor 15 on the left side, an image of the object (that is, living body) illuminated with illuminating light is displayed as the ordinary color observation image. In the present embodiment, the RGB image signal for one frame is outputted from the VRAM41 and an image based on this image signal is displayed on the monitor 15 every 1/30 second, for example. For this reason, on the display area of the monitor 15 on the left side, the ordinary color observation image is displayed as a moving picture. The operation of the video endoscopic apparatus 10 at the time of ordinary color image observation is thus complated. FIG. 5 shows an example of the ordinary color observation image comprising a hollow portion A and an inner wall portion B of a windpipe of a patient as the object. Although the inner wall portion B actually includes a tumor part C, this tumor part C can be hardly distinguished from the normal portion in the ordinary color observation image because the luminance distribution in the ordinary color observation image is as shown in FIG. 6.

Next, the operation of the video endoscopic apparatus 10 at the time of fluorescent diagnosis will be described. When the external switch 36a is turned on, the MIC35 of the video processor 13 detects a signal (ON signal) generated by this power-on to notify the PC14 (CPU38) of that effect. The CPU38 determines whether or not it was notified from the MIC35 that the ON signal was detected (S7) every time it complete executing the above-described processes of S1 through S6, and if not, the sequence will return to step S1. If affirmative, the processes for forming a fluorescent diagnosis image will be executed in step S8. FIG. 4 is a flow chart showing the subroutine of processes for forming a fluoresecnt diagnosis image to be executed in this step S8. In this subroutine, the CPU38 first stores the RGB image signal (that is, data of the ordinary color observation image) obtained last into the memory M1 (S101). In this case, it is assumed that data of the ordinary color observation image substantially same as the image shown in FIG. 5 has been stored in the memory M1.

Subsequently, the CPU38 gives the light source control unit 27 a control instruction for making the light source device 12 function in a fluorescent observation state (S102). Then, the light source control unit 27 in the light source device 12 inserts the first mirror 25 into the optical path of excitation light from the UV light source 24, and moves the second mirror 26 to the position where excitation light reflected by the first mirror 25 is caused to reflect toward the incident end face of the light guide 20. Subsequently, the CPU38 gives the MIC35 a control instruction to bring the switch piece of the switch SW into contact with the output terminal T2 and to start the amplifier 32 (S103). Receiving this instruction, the MIC35 brings the switch piece of the switch SW into contact with the output terminal T2, and imparts a control signal to the control terminal of the amplifier 32.

Figure 9:
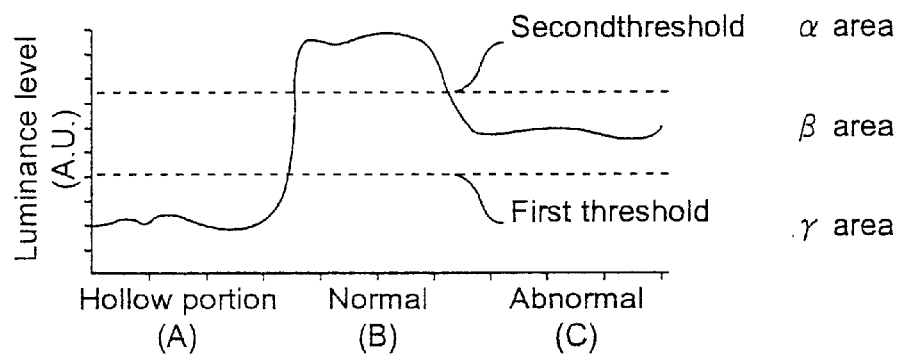
FIG. 9 is a graph showing luminance distribution in an auto-fluorescent image.

When the processes of S102 through S103 are executed, excitation light emitted from the UV light source 24 is reflected by the first mirror 25 and the second mirror 26, and is incident into the light guide 20. This excitation light is transmitted to the distal end part of the video endoscope 11 through the light guide 20, then emitted from the emitting end face of the light guide 20, and irradiated onto the object while being diffused by the light distribution lens 21. As a result, auto-fluorescent light is emitted from the organismic organization of the windpipe as the object. At this time, the intensity of component of light within wavelength band of a green light included in the auto-fluorescent light emitted from a normal part of the organismic organization is higher than the intensity of a green light band component included in the auto-fluorescent light emitted from the tumor part C. Light from the object including the auto-fluorescent light and reflected light of excitation light is incident on the objective optical system 18, and transmits through the cut-off filter 19. Since this cut-off filter 19 removes component of light in an ultraviolet band, only the component of auto-fluorescent light transmits through the cut-off filter 19 to form the object image on the pick-up surface of the CCD17. Thus, the CCD17 picks up an image of the object (living body) irradiated with excitation light, which is an auto-fluorescent image. At this time, since the intensity of auto-fluorescent light emitted from the normal part of the living body is higher than the intensity of auto-fluorescent light from the abnormal part, quantity of light received by each pixel of the CCD17 which has picked up a part of an image of the normal part becomes greater than an amount of light received of pixels which picked up an image in the tumor part C as shown in FIG. 9. Thus, the CCD17 outputs an image signal (F image signal) corresponding to the quantity of light received by the pixels. Thereafter, the F image signal is transmitted to the amplifier 32 through the signal cable 17a and the switch SW, then amplified by the amplifier 32, then converted from analog form to digital form by the A-D converter 33, and stored in the F memory 34. When the F image signal for one frame is thus stored in the F memory 34, the scan converter 36 outputs the F image signal inside the F memory 34 toward the PC14. Thus, the F image signal is stored in the video capture 39. Then, the CPU38 writes the F image signal (that is, data of auto-fluorescent image) which have been stored in the video capture 39 (S104) into the memory MF. In this way, concerning the substantially same pick-up range, the RGB image signal(that is, data of the ordinary color observation image) is stored in the memory M1, and the F image signal (that is, data of the auto-fluorescent light image) is stored in the memory MF.

Figure 7:
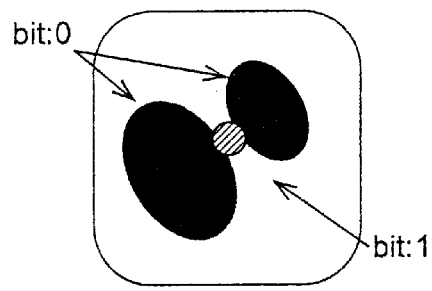
FIG. 7 is a view showing a display example of the ordinary color observation image after binarized on the basis of the first threshold.
Figure 8:
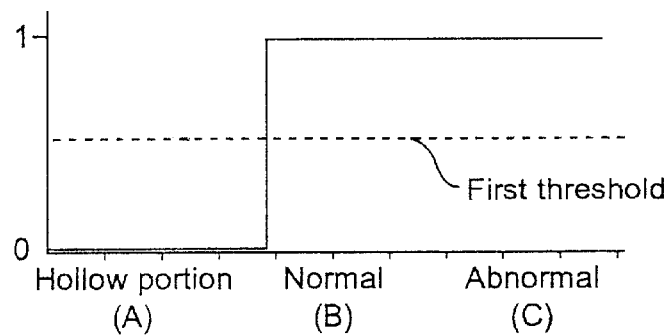
FIG. 8 is a graph showing luminance distribution in the ordinary color observation image after binarized on the basis of the first threshold.

Subsequently, the CPU38 executes, for every pixel of the RGB image signal stored in the memory M1 at this point of time, a predetermined matrix operation (that is, RGB-YCC converting operation) on luminance values of the R image signal, the G image signal and the B image signal composing the pixel to thereby calculate the luminance value (binary value represented by 8 bits) of the same pixel as a whole. The CPU38 writes luminance values (Y signal) which are calculated for all the pixels respectively in this way into the memory M2 (S105). As a result, the image signal stored in the memory M2 becomes such that the luminance in the hollow portion A is low and the luminance in the inner wall portion B including the tumor part C is high as shown in FIGS. 5 and 6. Next, the CPU38 binarizes the luminance value of each pixel of the image signal stored in the memory M2 by comparing it with a predetermined first threshold (indicated in broken line in FIG. 6 (S106). More specifically, the CPU38 rewrites all eight bits representing the luminance value of a pixel whose luminance value is lower than the first threshold to "0." On the other hand, the CPU38 rewrites all eight bits representing the luminance value of a pixel whose luminance value is higher than the first threshold to "1." As a result, as shown in FIGS. 7 and 8, the hollow portion A is distinguished from the inner wall portion B, and only pixels corresponding to the inner wall portion B comes to have luminance value of "11111111."

Figure 10:
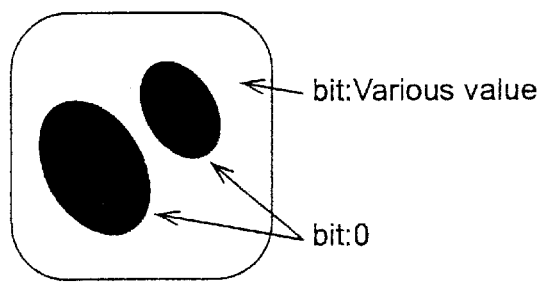
FIG. 10 is a view showing a display example of an auto-fluorescent image after logical processing.
Figure 11:
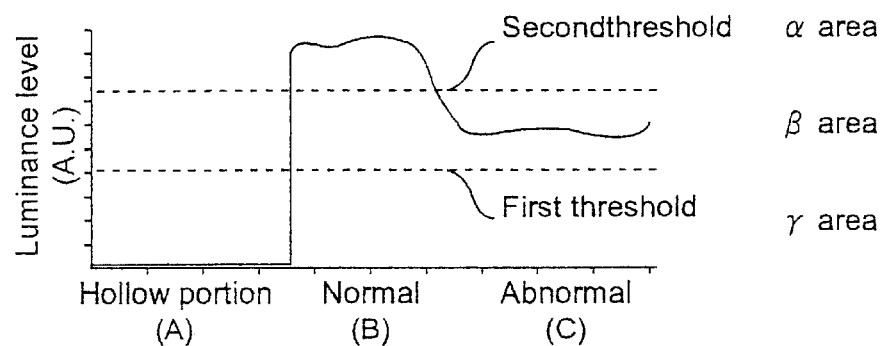
FIG. 11 is a graph showing luminance distribution in the auto-fluorescent image after the logical processing.

On the other hand, F image signal stored in the memory MF has a distribution of luminance values, each of which is a binary value represented by eight bits, as shown in FIG. 9. The CPU38 executes, for every pixel of image signal stored in memory M2, AND operation on value of each bit constituting luminance value of the pixel stored in the memory M2 and value of correspondent bit constituting luminance value of the pixel stored in the memory MF, and overwrites the result of the operation on the memory MF (S107). As a result, as shown in FIGS. 10 and 11, the image signal in which a portion corresponding to the hollow portion A is masked and in which only a portion corresponding to the inner wall portion B (including the tumor part C) remains as it was in F image signal is newly held in the memory MF. More specifically, as regards the luminance value of a pixel within the inner wall portion B of image signal stored in the memory MF, as shown in FIG. 11, the normal part is higher than the tumor part C.

Next, the CPU38 binarizes the luminance value of each pixel of the image signal stored in the memory MF by comparing it with a predetermined second threshold which is greater than the first threshold as indicated in broken line in FIG. 11 (S108). More specifically, the CPU38 rewrites all eight bits representing the luminance value of a pixel whose luminance values exist in β or γ area which is lower than the second threshold to "0." On the other hand, the CPU38 rewrites all eight bits representing the luminance value of a pixel whose luminance values exist in α area which is higher than the second threshold to "1." As a result, only the normal part are extracted from the inner wall portion B in the image signal, and only pixels corresponding to the normal part comes to have a luminance value "11111111."

Figure 12:
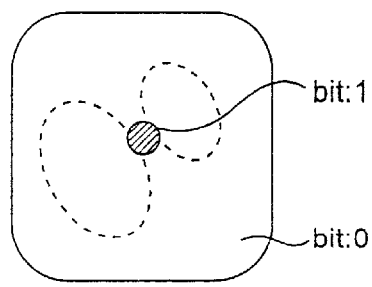
FIG. 12 is a view showing a display example of the auto-fluorescent image after binarized on the basis of the second threshold.
Figure 13:
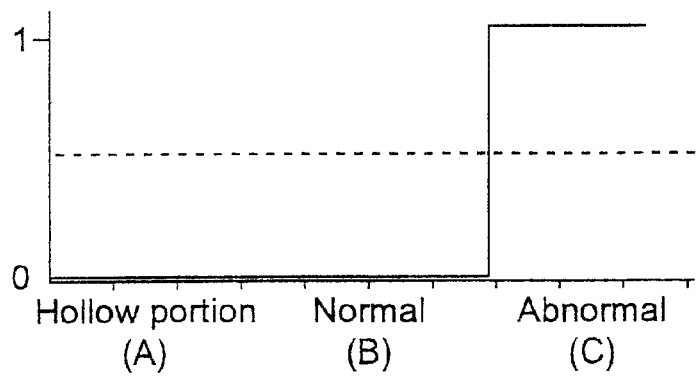
FIG. 13 is a graph showing luminance distribution in the auto-fluorescent image after binarized on the basis of the second threshold.

The CPU38 executes, for every pixel of image signal stored in the memory M2, exclusion OR operation on value of each bit constituting the luminance value of the pixel stored in the memory M2 and value of corresponding bit constituting the luminance value of the pixel stored in the memory MF, and overwrite the result of the operation on the memory M2 (S109). As a result, as shown in FIGS. 12 and 13, image signals showing the shape and position of the tumor part C are held in the memory M2.

Subsequently, the CPU38 writes image signal (data of ordinary color observation image) stored in the memory M1 into an area of the VRAM41 on the left side (S110). Next, the CPU38 generates a still image data indicating an image in which the ordinary color observation image and an image of the tumor part C determined on the basis of the intensity of the auto-fluorescent light are combined. In other words, the CPU38 specifies the pixels in the memory M1 which correspond to the pixels having luminance vale of "11111111" in the memory M2 and sets the color of the pixels thus specified to, for example, B (blue) in the memory M1 (S111). As a result, in the memory M1, there are generated the still image data of the fluorescent diagnosis image in which an area corresponding to the tumor part C (abnormal part) within the ordinary color observation images is indicated in blue. The CPU38 writes the data of fluorescent diagnosis image stored in the memory M1 into an area of the VRAM41 on the right side (S112). When the entire VRAM41 is filled with image data as described above, the CPU38 makes the contents of the VRAM 41 (that is, image data showing picture to be displayed on the monitor 15) outputted toward the D-A converter 37 (S113).

The contents of the VRAM41 are supplied to the monitor 15 through the D-A converter 37, so that the fluorescent diagnosis image in which the tumor part C is indicated in blue is displayed on the display area on the right side.

Figure 14:
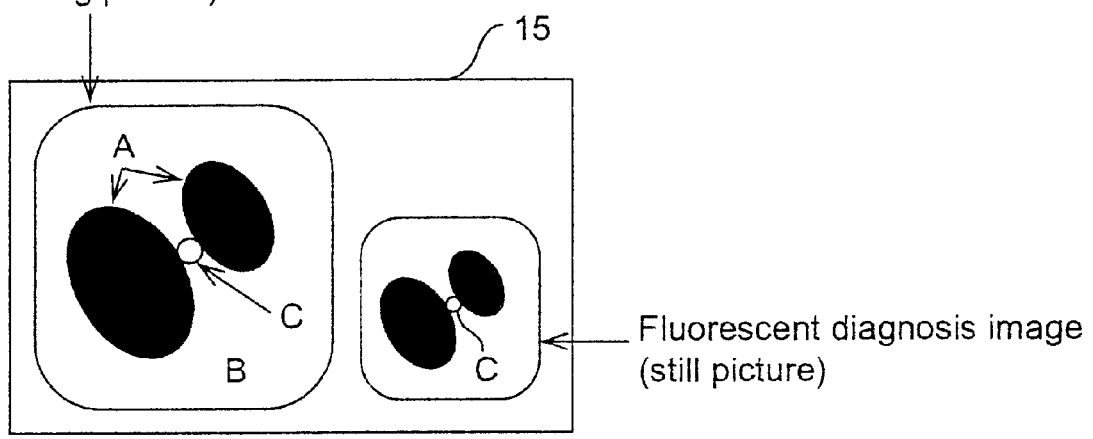
FIG. 14 is a view showing an example of screen displayed on the monitor.

Thereafter, the CPU38 gives the light source control unit 27 and the MIC35 a control instruction to operate the light source device 12 and the video processor 13 in the color observation state (S114), and terminates this subroutine. On receipt of the control instruction in S114, the MIC35 brings the switch piece of the switch SW into contact with the output terminal T1. At the same time, the light source control unit 27 retracts the first mirror 25 and the second mirror 26 to the respective positions shown by dotted line in FIG. 1. As a result, the video endoscopic apparatus 10 functions in ordinary color image observation state again, and the ordinary color observation image displayed on the display area on the left side of the monitor 15 becomes a moving picture, as shown in FIG. 14.

Usage of Video Endoscopic Apparatus

The description will be made of an example of usage of a video endoscopic apparatus 10 as described above. First, an operator of the video endoscopic apparatus 10 turns on the power supply for the light source 12, the video processor 13, the PC14, and the monitor 15. Then, the CPU38 in the PC14 starts to execute the main routine shown in FIG. 3, so that a ordinary color observation image of an object is displayed on the display area of the monitor 15 on the left side.

Subsequently, the operator inserts the insertion portion 16 of the video endoscope 11 into the body cavity and searches for a part which is expected to be the tumor part C while observing the ordinary color observation image displayed on the monitor 15.

Thereafter, when a part which is expected to be the tumor part C is displayed on the monitor 15 (See FIG. 5), the operator turns on the external switch 36a. Then, the CPU38 in the PC14 executes the processes for forming a fluorescent diagnosis image shown in FIG. 4, so that a fluoresecnt diagnosis image is displayed on the display area of the monitor 15 on the right side.

At this time, if there is an area displayed in blue on the fluorescent diagnosis image, there is a high possibility that the part which is expected to be the tumor part C is actually a tumor part. On the other hand, if there is no area displayed in blue, there is a high possibility that the part which is expected to be the tumor part C is a normal part. Thus, the operator diagnoses, on the basis of the ordinary color observation image and the fluorescent diagnosis image displayed side by side, whether or not the part which is expected to be the tumor part C is actually a tumor part.

Effect of the Embodiment

In accordance with the video endoscopic apparatus 10 of the present embodiment, if the operator turns on the external switch 36a at the point when image of a part which is expected to be the tumor part C, the CPU38 in the PC14 extracts the tumor part C (part consisting of pixels whose luminance values belong to the β area) from the auto-fluorescent image on the basis of an intensity difference in the auto-fluorescent image and displays a fluorescent diagnosis image in which the tumor part C is indicated in blue, on the monitor 15. Therefore, the operator can appropriately diagnose whether or not the part which is expected to be the tumor part C is actually a tumor part.

Also, in accordance with the video endoscopic apparatus 10 of the present embodiment, it is possible to display a fluorescent diagnosis image appropriately indicating the tumor part C on the monitor 15 even if no image intensifier is provided. For this reason, the video endoscopic apparatus 10 can be easily constructed with reduction of the cost. Particularly, since it is not necessary to arrange an image intensifier at the distal end of the insertion portion of the video endoscope, it is possible to prevent the distal end from becoming larger, which makes it possible to reduce a load of pain imposed on a patient.

In this respect, in accordance with the present embodiment, a fluorescent diagnosis image in which an area corresponding to the tumor part (part whose luminance values belong to the β area in the auto-fluorescent image) within the ordinary color observation image stored in the memory M1 is indicated in blue is displayed on the monitor 15. However, it may be possible to display, on the monitor 15, a fluorescent diagnosis image in which the tumor part within the auto-fluorescent image stored in the memory MF is indicated in blue.

Also, in accordance with the present embodiment, an output signal from the CCD17 at the time of a fluorescent diagnosis is amplified by the amplifier 32, but it may be possible to amplify an output signal from the CCD17 by the use of frame addition processing in place of amplification by the amplifier 32.

We claim:

1. A video endoscopic apparatus for fluorescent diagnosis, comprising:

an image pick-up device that senses an auto-fluorescent image generated by irradiating a living body with excitation light, and an ordinary color observation image;

a detection unit that detects a specific area where a luminance value is within a predetermined range from said auto-fluorescent image sensed by said image pick-up device, wherein said detection unit extracts an area where said luminance value is higher than a predetermined first threshold from said ordinary color observation image and extracts an area where said luminance value is lower than a predetermined second threshold from said auto-fluorescent image; and a display control device that outputs an image signal indicating said specific area.

2. The video endoscopic apparatus of claim 1, further comprising an illuminating device that selectively emits illuminating light in a visible band and said excitation light in a ultraviolet band to irradiate the living body, said image pick-up device sensing an ordinary color observation image of said living body irradiated with said illuminating light in the visible band and said auto-fluorescent image of said living body irradiated with said excitation light, and wherein said detection unit detects, from the area extracted from said ordinary color observation image, an area included in the area extracted from the auto-fluorescent image as said specific area.

3. The video endoscopic apparatus for fluorescent diagnosis according to claim 2, wherein said display control device outputs an image signal for displaying a fluorescent observation image, in which only said specific area is displayed in a predetermined color and the other area is displayed as they are in said ordinary color observation image.

4. The video endoscopic apparatus of claim 3, wherein said illuminating device irradiates the living body with red illuminating light, green illuminating light and blue illuminating light emitted from the illuminating device, and at the same time, picks up images of said living body respectively irradiated with each illuminating light, and wherein said display control device synthesizes said ordinary color observation image on the basis of the images of said living body irradiated with said respective illuminating light, and generates a specific area image of said specific area extracted from said auto-fluorescent image and outputs an image signal for displaying a fluorescent observation image comprising said specific area image superimposed on said ordinary color observation image.

5. The video endoscopic apparatus for fluorescent diagnosis according to claim 4, wherein said display control device outputs image signal for displaying both of said ordinary color observation image and said fluorescent observation image at the same time.

6. The video endoscopic apparatus for fluorescent diagnosis according to claim 5, further comprising a switch, which is operated by an operator to generate a switching signal, said switching signal causing said display control device to output an image signal for displaying only said ordinary color observation image or an image signal for displaying said ordinary color observation image and said fluorescent diagnosis image at the same time selectively.

7. The video endoscopic apparatus for fluorescent diagnosis according to claim 2, wherein said display control device outputs an image signal for displaying said ordinary color observation image as a moving picture.

8. The video endoscopic apparatus for fluorescent diagnosis according to claim 1, wherein said display control device outputs an image signal for displaying a fluorescent observation image, in which only said specific area is indicated in a predetermined color.

9. The video endoscopic apparatus of claim 1, wherein the detection unit extracts a first area where a luminance value is higher than said predetermined first threshold from said auto-fluorescent image and extracts, as said specific area, a second area where said luminance value is lower than said predetermined second threshold from said first area extracted by said detection unit.

* * * * *

UNITED STATES PATENT AND TRADEMARK OFFICE
CERTIFICATE OF CORRECTION

PATENT NO.    : 6,371,908 B1
DATED         : April 16, 2002
INVENTOR(S)   : K. Furusawa et al.

It is certified that error appears in the above-identified patent and that said Letters Patent is hereby corrected as shown below:

<u>Title page,</u>
Item [56], References Cited, the following U.S. PATENT DOCUMENTS should be inserted: -- 5,749,830   5/1998         Kaneko et al. --; and
The following FOREIGN PATENT DOCUMENTS should be inserted:
-- HEI 9-070384       3/1997        JP
   HEI 7-155292       6/1995        JP --

Signed and Sealed this

Fifteenth Day of October, 2002

*Attest:*

JAMES E. ROGAN
*Attesting Officer*                  *Director of the United States Patent and Trademark Office*